US00PP31580P3

(12) United States Plant Patent
Chang

(10) Patent No.: US PP31,580 P3
(45) Date of Patent: Mar. 24, 2020

(54) STRAWBERRY PLANT NAMED 'AMERICAN AROMA 10'

(50) Latin Name: ***Fragaria xananassa* Duchesne**
Varietal Denomination: American Aroma 10

(71) Applicant: Peggy Pai-Chi Chang, Naples, FL (US)

(72) Inventor: Peggy Pai-Chi Chang, Naples, FL (US)

(73) Assignee: Peggy Pai-Chi Chang, Naples, FL (US)

( * ) Notice: Subject to any disclaimer, the term of this patent is extended or adjusted under 35 U.S.C. 154(b) by 71 days.

(21) Appl. No.: 15/998,360

(22) Filed: Aug. 8, 2018

(65) Prior Publication Data

US 2020/0053928 P1 Feb. 13, 2020

(51) Int. Cl.
*A01H 5/08* (2018.01)
*A01H 6/74* (2018.01)

(52) U.S. Cl.
USPC ..... Plt./208
CPC ..... *A01H 6/7409* (2018.05)

(58) Field of Classification Search
USPC ..... Plt./208, 209
CPC ..... A01H 5/0893
See application file for complete search history.

*Primary Examiner* — Kent L Bell

(57) ABSTRACT

'American Aroma 10' is a new and distinct short-day cultivar of strawberry plant, which produces large, sweet and firm fruits with glossy red color. The new cultivar has a healthy plant with large, firm fruit similar to 'Treasure Harvest' (U.S. Plant Pat. No. 19,422) but is sweeter in flavor like 'Treasure' (U.S. Plant Pat. No. 12,414). 'American Aroma 10' is resistant to strawberry anthracnose fruit rot which is an improvement from 'Treasure' which is a good characteristic for organic growers. 'American Aroma 10' has high yield but is not as early as 'Treasure' when produced in central and south Florida. Because of its good fruit quality, firmness, long shell life and healthiness 'American Aroma 10' is recommended for fresh market in the Southeastern United States, especially for organic growers.

2 Drawing Sheets

Latin name: *Fragaria xananassa* Duchesne.

Varietal denomination: 'American Aroma 10'.

'American Aroma 10' is a new and distinct short-day cultivar of strawberry plant, which produces large, sweet and firm fruits with glossy red color. The new cultivar has a healthy plant with large, firm fruit similar to 'Treasure Harvest' (U.S. Plant Pat. No. 19,422) but is sweet in flavor like 'Treasure' (U.S. Plant Pat. No. 12,414). 'American Aroma 10' is resistant to strawberry anthracnose fruit rot which is a good characteristic for organic growers and an improvement from 'Treasure'. 'American Aroma 10' has high yield when produced in central and south Florida, but is not as early as 'Treasure'. Because of its good fruit quality, firmness, long shell life and healthiness 'American Aroma 10' is recommended for fresh market in the Southeastern United States, especially for organic growers.

BACKGROUND OF THE INVENTION

The invention of 'American Aroma 10', a new and distinctive cultivar of strawberry plant, botanically identified as *Fragaria xananassa* Duch., which is a result of cross breeding 'A7' (an unpatented selection) and 'Treasure Harvest' (U.S. Plant Pat. No. 19,422). It was selected in a controlled breeding plot at a cultivated field located in Naples, Fla. during the fruiting season of 2009-2010 and was designated as 9047-105 by the inventor. The female parent 'A7' is a large healthy plant with large leaves which is resistant to anthracnose crown rot, powdery mildew, botrytis fruit rot, cyclamen mites, cracking from rain and has many good characteristics such as high yield, good fruit quality, very large fruit size, conic fruit shape, glossy fruit color and very good flavor, but lacks fruit firmness. The male parent 'Treasure Harvest' is a healthy, vigorous plant type which is resistant to anthracnose crown rot and anthracnose fruit rot, and has high yield, stable production, long storage shelf life, large fruit size, and firm fruit. 'American Aroma 10' obtains many good characteristics from the female parent 'A7' including good flavor and high tolerance to powdery mildew and botrytis fruit rot. It obtains other good characteristics from the male parent 'Treasure Harvest' including a healthy and vigorous plant, resistance to anthracnose fruit rot, stable production, long shelf life and firm fruit. Characteristics obtained from both parents include resistance to anthracnose crown rot, high yield, and large fruit size. Beside these characteristics 'American Aroma 10' surpasses its parents in sweetness of the fruit and aromatic flavor. 'American Aroma 10' has been propagated asexually by runner in Naples, Fla. since 2009-2010 as well as in commercial nurseries in the United States and Canada. It has been trialed in the fields of growers in Florida. 'American Aroma 10' plant retains its distinctive characteristics and asexually reproduces true to type in successive generations.

COMPARISON TO CLOSEST CULTIVARS

Of the commercial cultivars known to us, we believe 'Treasure Harvest' (U.S. Plant Pat. No. 19,422) to be the closest in appearance and 'Treasure' (U.S. Plant Pat. No. 12,414) to be closest in flavor to 'American Aroma 10'. Because 'Treasure Harvest' (U.S. Plant Pat. No. 19,422) was only used commercially for a short period of time, we used 'Treasure' (U.S. Plant Pat. No. 12,414) which is used in Florida as the comparison cultivar and 'Florida Radiance' (U.S. Plant Pat. No. 20,363) which is the dominant cultivar in the state of Florida for yield comparison. However, there are several characteristics of 'American Aroma 10' that are different from or not possessed by 'Treasure'. Those are:

(1). Size: The fruit size of 'American Aroma 10' is distinguishable larger when compared with 'Treasure'.

(2). Firmness: The fruit of 'American Aroma 10' is distinguishable firmer when compared with 'Treasure'.

(3). Plant size: The plant size of 'American Aroma 10' is distinguishable larger than that of 'Treasure'.

(4). Anthracnose fruit rot resistance: The plant of 'American Aroma 10' has exhibited resistance to anthracnose fruit rot disease (caused by *Colletotrichum acutatum*), which is one of the major diseases in strawberries grown in the Southeastern United States. In comparison, 'Treasure' is susceptible to anthracnose fruit rot disease.

DNA of leaf samples of 'American Aroma 10' were tested with SSR markers showing the fingerprint of 'American Aroma 10' is different from other strawberry commercial varieties from public and private sources in the database.

DESCRIPTION OF THE FIGURES

The following pictures show a typical specimen of the plant and fruit as seen in February to March in west central Florida and Naples, Fla.

FIG. 1 depicts a) a typical mature compound leaf, b) a representative complete flower during the mid-fruiting season, c) a partial fruiting truss including different stages of flowering and fruiting, and d) a typical mature fruit.

SUMMARY OF THE NEW CULTIVAR

Figure 1:
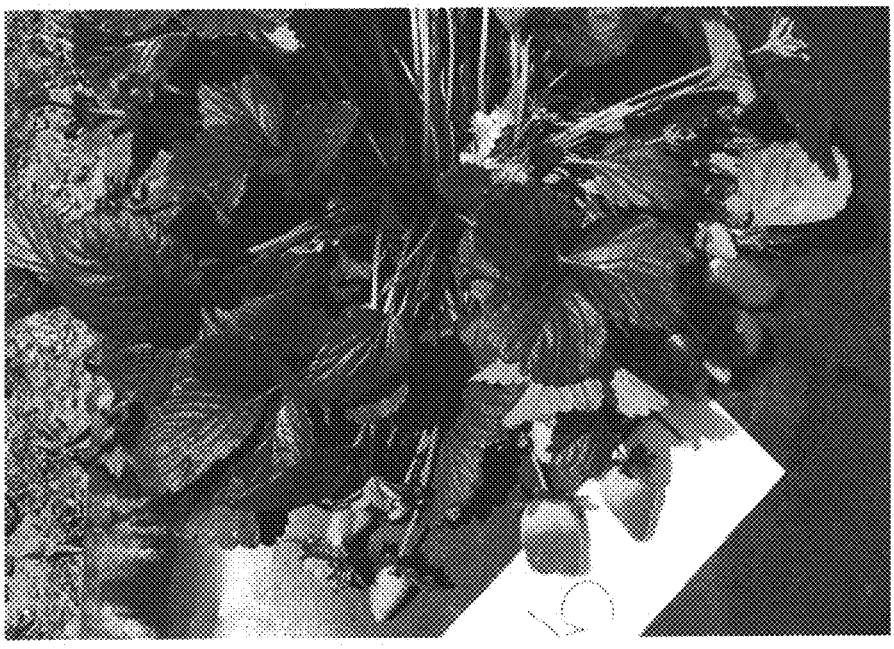
FIG. 1 shows the general growth, flowering and fruiting characteristics of the plants during mid-season fruit production in late February which is 4-5 months after planting in Florida.
Figure 2:
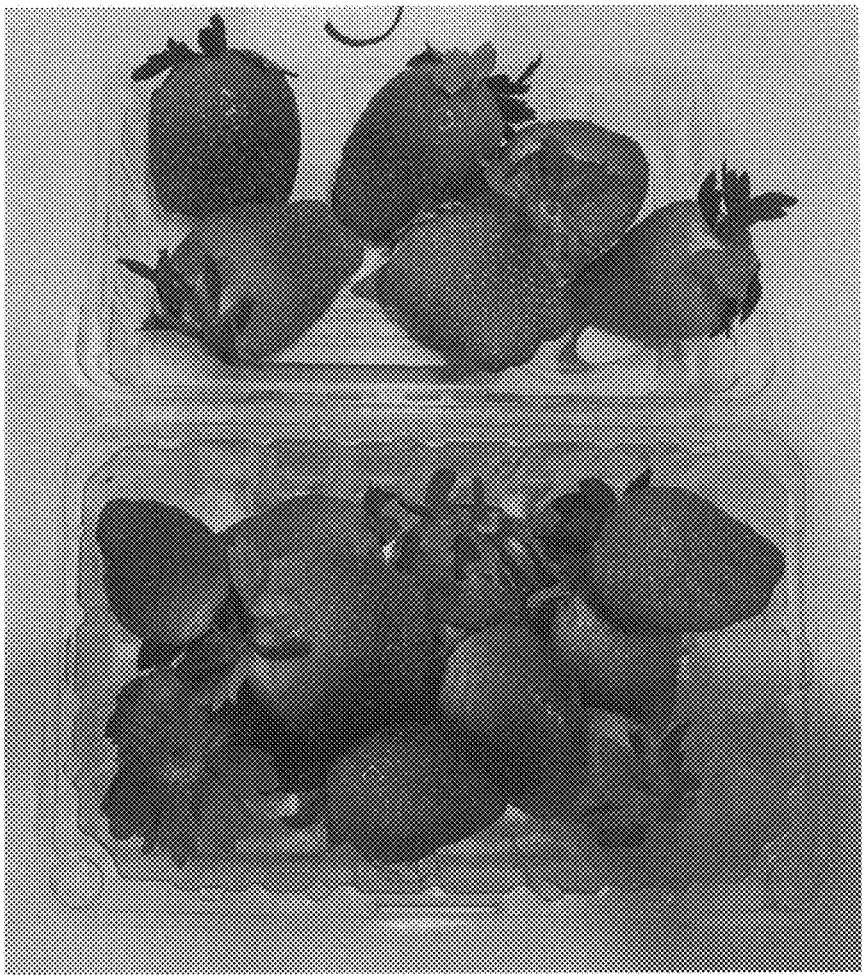
FIG. 2 shows plural fruit of one pound clam shell reflecting the variation in fruit shape and size within market grade and shows seed and calyx placement relative to the fruit surface, as well as the attractive and uniform coloration of the ripe fruit at harvest stage.

The new cultivar 'American Aroma 10' is a short-day type plant with characteristics including a healthy and vigorous plant, resistance to anthracnose crown rot, high and stable production, large firm fruit, very sweet and excellent flavor, glossy color and a long shelf life.

PLANTS AND FOLIAGE

The characteristics of this new strawberry variety, described in detail below were for typical vigorous mature plants with distinctive dark green leaves grown under warm day and cool night weather condition, observed during February to March in Naples, Fla. The color is objectively described using Munsell Color Chart for plant tissues.

Table 1: Plant & Foliage characteristics for 'American Aroma 10'.

Plant.

Number of crowns per plant: 5-10.

Average size:

*Height* (*mm*).—202.

*Diameter* (*mm*).—357.

Shape: Globose.

Density: Medium to open.

Vigor: Strong.

Root initiation: Good rooting, about 5 days to 1 week.

Foliage.

Number of leaflets per leaf: 3.

Terminal leaflet:

*Length* (*mm*).—59.

*Width* (*mm*).—53.

Shape of terminal leaflet: Orbicular with serrulate margin.

Color (Munsell color charts) of terminal leaflet:

*Apex.*—Dark green 5GY 3/4.

*Base.*—Medium green 5GY 5/4.

Leaf pubescence: Moderate and direction is acropetal.

Serrations number of terminal leaflets (mean): 17.

Petiole: No plant's stipule has been found at the petiole.

*Length* (*mm*).—143.

*Diameter* (*mm*).—3.

*Color* (*Munsell color charts*).—Light grey green 5GY 7/6.

Petiolule:

*Length* (*mm*).—11.

*Diameter* (*mm*).—1.8.

*Color* (*Munsell color charts*).—Light green 5GY 7/8.

Base angles of terminal leaflets (half blade) (degree): 54.

Stolons:

*Length* (*mm*).—380.

*Thickness* (*diameter, mm*).—3.

*Number.*—Produced about 20-50 per plant, average 30.

*Pubescence.*—Moderate and direction is acropetal.

Resistance to disease: The plant of 'American Aroma 10' has been observed from 2010 to 2018 at the fruiting field in Naples, Fla. and grower trials in Plant City, Fla. during 2016-2017 & 2017- 2018 seasons, showing resistance to strawberry anthracnose crown rot and anthracnose fruit rot.

Flowering and fruiting characteristics: The distinguishing flowering and fruiting characteristics of 'American Aroma 10' plants collected during February to March about 4-5 months after planting are presented in Table 2. The flowers are self-fertile and pollination is excellent. The center of the fruit is solid with little to no hollowing. It typically begins to harvest about seven to seven and a half weeks after planting in Florida commercial production areas.

Table 2: Flower and fruit characteristics for 'American Aroma 10'.

Bud: At the stage of largest size, 1 day before flower opens.

*Diameter* (*mm*).—35.

*Length* (*mm*).—19.

*Base shape of flower bud.*—Acute.

*Color* (*Munsell color charts*).—Upper: Medium green 5GY 5/6. Base: Medium light green 5GY 6/6.

Flower: At fully open stage, 1 day after starting to open.

*Diameter* (*mm*).—40.

*Depth* (*Height*) (*mm*).—171.

*Number of flowers/cluster.*—3 to 6.

*Number of clusters/crown.*—1 to 3.

*Number of crowns/plant.*—5 to 10.

*Fragrance.*—None.

Bloom time and period in specific location: Observed at the research plots in Naples, Fla., plants were planted in mid-October and the earliest buds started opening 4 weeks after planting. Plants bloom from November until May.

Petals:

*Length* (*mm*).—9.

*Width* (*mm*).—8.3.

*Shape.*—Obtuse. Apex: Obtuse. Base: Obtuse.

*Color.*—White 5GY 9/1.

*Texture.*—Smooth.

*Margin.*—Entire.

*Number.*—Mean: About 7. Range: 7-8.

Sepals (Calyx):

*Diameter* (*mm*).—13.

*Width* (*mm*).—6.3.

*Shape.*—Oblanceolate. Apex: Acute. Base: Cuneate. Margin: with teeth.

*Color* (*Munsell color charts*).—Abaxial: Medium dark green 5GY4/6. Adaxial: Medium light green 5GY 6/4.

*Number.*—Mean: 15. Range: 14-16.

Reproductive organs:

*Stamens.*—Number: 24-34. Length (mm): 2-5.5. Color (Munsell color charts): Bright yellow 5Y 8/10.

*Pistils.*—Number & location: About 200-450 pistils attached on the surface of the receptacle. Length (mm): 1.8. Color (Munsell color charts): Yellow 2.5Y 8/12.

Fruit shape) Long Conic and wedge.

Fruit size & color:

*Development stage.*—Green fruit: At maximum size about 1-2 days before starting to turn pink. Size: Length (mm): 45. Diameter (mm): 30. Color (Munsell color charts) Exterior: light green 2.5GY8/6. Interior: almost white 2.5GY9/2. Pink fruit: About 1-2 days before red. Size: Length (mm): 43. Diameter (mm): 33. Exterior: 7.5R6/12. Interior: 7.5R7/10. Ripe fruit-red: About 1-2 days after pink. Size: Length (mm): 44-51. Diameter (mm): 36-37. Weight (gram/fruit): Average: 31. Primary: 36. Color (Munsell color charts): Exterior: Glossy good red 7.5R4/16. Interior: 7.5R4/12. The fruiting truss: Length (mm) — 255. Diameter (mm) — 4. Number of berries per truss: 3 to 6 fruits/truss.

Firmness of fruit: The firmness of fruit measured by fruit pressure tester equipped with 3 mm diameter plunger tip: Mean.—820. Range.—600-1005.

Sugar content of fruit: The sugar content or sweetness, measured as soluble solids, Mean.—9.6. Range.—7.4-13.

Pedicel:

*Of flowers.*—Flower at fully open stage. Length (mm): 79. Diameter (mm): 1.9. Color (Munsell color charts): Light green 5GY 7/8.

*Of fruits.*—Red ripe fruit stage. Length (mm):123. Diameter (mm): 2.5. Color (Munsell color charts): Medium light green 5GY6/6.

Seeds:

*Number* (*mean*)/*fruit.*—403.

*Shape.—Oblong.*

*Size.*—length (mm): 1-1.5. diameter (mm): 0.5-1.

*Color* (*Munsell color charts*).—Medium yellow 2.5Y 8/8 — Medium red 5R 5/10.

Calyx position: Even/slight indent.

Seed position: Even with skin. The yield of 'American Aroma 10' is compared with those of 'Treasure' and 'Florida Radiance' in Table 3.

TABLE 3

Data on yield obtained from the 2016-17 & 2017-18 fruiting season in Naples, Florida.
Marketable yield (grams/plant)

| Cultivar | December | January | February | March | April | Total |
|---|---|---|---|---|---|---|
| 2016-17 (harvested until Apr. 11, 2017) | | | | | | |
| 'American Aroma 10' | 4.6 | 45.1 | 128.9 | 152.7 | 31.6 | 362.9 |
| 'Treasure' | 14.9 | 74.0 | 103.0 | 101.3 | 17.9 | 311.1 |
| 'Florida Radiance' | 53.1 | 52.4 | 70.8 | 83.0 | 15.8 | 275.1 |
| 2017-18 (harvested until Mar. 9, 2018) | | | | | | |
| 'American Aroma 10' | 14.0 | 58.5 | 160 | 62.2 | | 294.7 |
| 'Treasure' | 37.7 | 46.3 | 168.9 | 42.2 | | 295.1 |

As shown in Table 3, total yield of 'American Aroma 10' is equal or higher than 'Treasure' and much higher than 'Florida Radiance' which is currently the dominant cultivar in the state of Florida.

We claim:

1. A new and distinct cultivar of strawberry plant named 'American Aroma 10', as herein described and illustrated.

* * * * *